(12) United States Patent
Ruch et al.

(10) Patent No.: US 9,732,201 B2
(45) Date of Patent: Aug. 15, 2017

(54) NIR-INERT SUBSTRATES COMPRISING BIS-OXODIHYDROINDOLYLEN-BENZODIFURANONES

(71) Applicant: BASF SE, Ludwigshafen (DE)

(72) Inventors: Thomas Ruch, Delémont (CH); Philippe Bugnon, Le Mouret (CH); Paul Brown, Binzen (DE); Véronique Hall-Goulle, Dornach (CH)

(73) Assignee: BASF SE, Ludwigshafen (DE)

( * ) Notice: Subject to any disclaimer, the term of this patent is extended or adjusted under 35 U.S.C. 154(b) by 153 days.

(21) Appl. No.: 14/610,432

(22) Filed: Jan. 30, 2015

(65) Prior Publication Data

US 2015/0147493 A1  May 28, 2015

Related U.S. Application Data

(63) Continuation of application No. 12/669,049, filed as application No. PCT/EP2008/059265 on Jul. 16, 2008, now abandoned.

(30) Foreign Application Priority Data

Jul. 19, 2007 (EP) ..................... 07112790

(51) Int. Cl.
*B05D 5/00* (2006.01)
*C08K 5/54* (2006.01)
(Continued)

(52) U.S. Cl.
CPC .............. *C08K 5/3417* (2013.01); *B05D 7/52* (2013.01); *B32B 37/04* (2013.01); *B32B 37/182* (2013.01);
(Continued)

(58) Field of Classification Search
CPC ................................... C08K 5/3417
See application file for complete search history.

(56) References Cited

U.S. PATENT DOCUMENTS 4,772,725 A   9/1988  Altermatt
5,962,143 A   10/1999 Krauthauser et al.
(Continued)

FOREIGN PATENT DOCUMENTS

DE   3111650   1/1982
DE   3311375   10/1984
(Continued)

OTHER PUBLICATIONS

English language machine translation of DE 3111650 (1982).
(Continued)

*Primary Examiner* — Monique Jackson
(74) *Attorney, Agent, or Firm* — Marshall, Gerstein & Borun LLP

(57) ABSTRACT

A method for producing infra-red inert substrates, including molded polymeric articles, films, fibers and coatings and other organic and inorganic materials, by incorporating into the substrate or onto the surface of the substrate an effective amount of a dispersed bis-oxodihydroindolylen-benzodifuranone colorant. The thus obtained, also claimed substrates so produced are reflective and transparent to much of the near infra red radiation not reflected. There are multiple applications for cases of devices comprising electronic components, outdoor construction elements, outdoor furniture, automotive, marine or aerospace parts, laminates, artificial leather or textile materials, as well as in polychrome printing processes and optical fibers. The thus obtained substrates can also be subjected to laser welding. New bis-oxo-dihydroindolylen-benzodifuranone compounds are also claimed.

17 Claims, 2 Drawing Sheets

(51) Int. Cl.

| | |
|---|---|
| *C08K 5/3417* | (2006.01) |
| *B05D 7/00* | (2006.01) |
| *C07D 493/04* | (2006.01) |
| *C09B 57/00* | (2006.01) |
| *C09B 67/08* | (2006.01) |
| *C09D 5/02* | (2006.01) |
| *C09D 5/03* | (2006.01) |
| *C09D 7/00* | (2006.01) |
| *C09D 11/037* | (2014.01) |
| *C09D 11/18* | (2006.01) |
| *C09D 11/322* | (2014.01) |
| *B32B 37/04* | (2006.01) |
| *B32B 37/18* | (2006.01) |
| *B32B 38/00* | (2006.01) |
| *B05D 5/06* | (2006.01) |

(52) U.S. Cl.
CPC ........ *B32B 38/0008* (2013.01); *C07D 493/04* (2013.01); *C09B 57/00* (2013.01); *C09B 67/0013* (2013.01); *C09D 5/028* (2013.01); *C09D 5/035* (2013.01); *C09D 7/007* (2013.01); *C09D 11/037* (2013.01); *C09D 11/18* (2013.01); *C09D 11/322* (2013.01); *B05D 5/06* (2013.01); *Y10T 428/13* (2015.01); *Y10T 428/1372* (2015.01); *Y10T 428/24802* (2015.01); *Y10T 428/25* (2015.01); *Y10T 428/31504* (2015.04); *Y10T 428/31678* (2015.04)

(56) References Cited

U.S. PATENT DOCUMENTS

| | | |
|---|---|---|
| 6,171,383 B1 | 1/2001 | Sakoske et al. |
| 6,221,147 B1 | 4/2001 | Sakoske et al. |
| 6,503,937 B1 | 1/2003 | Nesvadba et al. |
| 6,989,056 B2 | 1/2006 | Babler |
| 2003/0083407 A1 | 5/2003 | Connor et al. |
| 2003/0121113 A1* | 7/2003 | Nesvadba ............ C07D 405/04 8/690 |

FOREIGN PATENT DOCUMENTS

| | | |
|---|---|---|
| DE | 301159 | 10/1992 |
| DE | 19540682 | 5/1997 |
| EP | 0279774 | 5/1988 |
| EP | 1217044 | 6/2002 |
| JP | 2002-249676 A | 9/2002 |
| WO | WO-99/13007 A1 | 3/1999 |
| WO | 00/24736 | 5/2000 |
| WO | 01/32577 | 5/2001 |

OTHER PUBLICATIONS

English language machine translation of DE 3311375 (1984).
Thompson Scientific AN#2002-409170[44] of JP 2002 020647 (2002).
Thompson Scientific AN#2001-619878[72] of JP 2001 152096 (2001).
Examination Report, Indian patent application No. 344/CHENP/2010, dated Dec. 21, 2016.
Notification of Reasons for Refusal (English translation), Japanese patent application No. 2010-516494, dated Apr. 30, 2013.

* cited by examiner

Fig. 1A
Fig. 1B
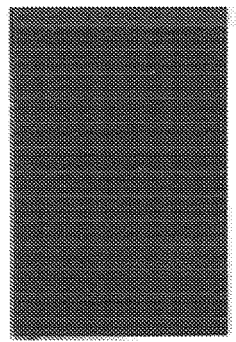
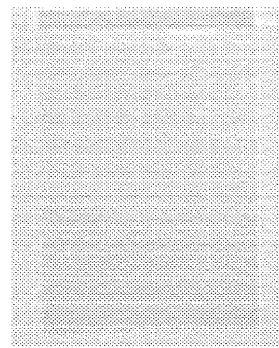
Fig. 2
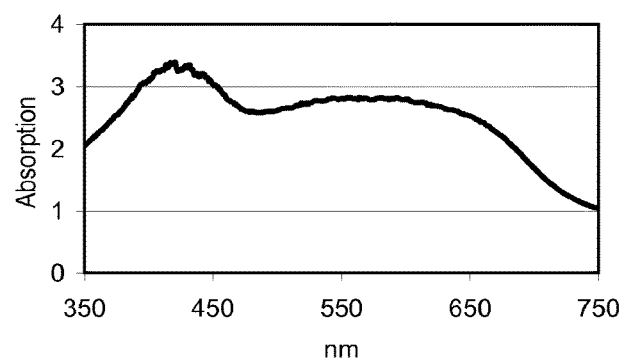
Fig. 3A
Fig. 3B
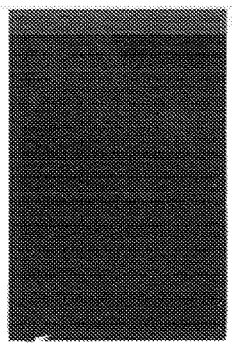
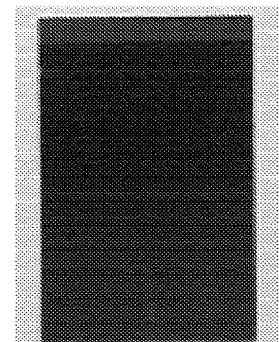

NIR-INERT SUBSTRATES COMPRISING BIS-OXODIHYDROINDOLYLEN-BENZODIFURANONES

CROSS-REFERENCE TO RELATED APPLICATIONS

This application is a continuation of U.S. patent application Ser. No. 12/669,049 filed on Jan. 14, 2010, which is a National Stage of International Application PCT/EP08/59265 filed Jul. 16, 2008, which claims priority to EP 07112790.6 filed Jul. 19, 2007, wherein the contents of all applications are herein incorporated by reference.

FIELD OF THE INVENTION

The invention belongs to a method for producing near infra-red inert substrates, including moulded polymeric articles, films, fibers and coatings and other organic and inorganic materials, by incorporating into the substrate or onto the surface of the substrate an effective amount of a bis-oxodihydroindolylen-benzodifuranone colourant. The colourants of the invention have the added property of being transparent to much of the near infra-red (NIR) radiation not reflected. Thus, very little NIR radiation is absorbed by these darkly colored colourants, further limiting heat build up and allowing for the production of laser welded articles.

BACKGROUND OF THE INVENTION

Materials which possess near infra-red (NIR) reflectance characteristics have proven to be valuable in many current applications. Such materials reduce NIR-induced heat buildup and find use in automotive and marine coatings, containers, colored plastics such as vinyl sidings, etc. Thermally robust compositions also find use in inorganic and organic glazing and aerospace, architectural and other glass and ceramic decorative applications where reduced heat buildup is desired.

Other applications which make use of NIR reflective materials include protective camouflage for military applications.

U.S. Pat. No. 6,171,383 and U.S. Pat. No. 6,221,147, both hereby incorporated in their entirety by reference, disclose IR reflective bismuth manganese oxide green pigments with improved heat buildup properties.

U.S. Pat. No. 6,989,056, hereby incorporated in its entirety by reference, discloses IR reflective black pigment compositions containing a halogenated copper phthalocyanine and a perylenetetracarboxylic acid diimide.

DE 31 11 650 and DE 33 11 375 disclose greenish, reddish or bluish black isoindolin colourants having a high IR remission.

US 2003/0 083 407 discloses polymeric articles comprising red, violet, blue or brown bismethine benzodifuranone colourants and teaches away from the isatin-based based benzodifuranones of WO 00/24 736, which discloses the compound of formula

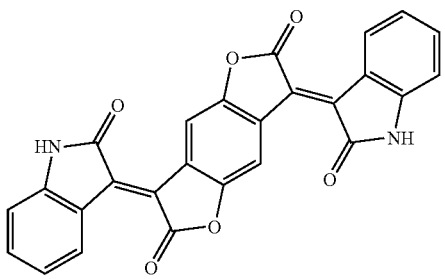 [SMILES: O=C1Nc2ccccc2/C1=C1\C(=O)Oc2cc3c(cc21)OC(=O)/C3=C1/C(=O)Nc2ccccc21]

(example 12b).

EP 1 217044 discloses near infra red reflecting composite pigments comprising a white pigment coated with a near infra red transmitting organic pigment, particularly preferred the black pigment of formula

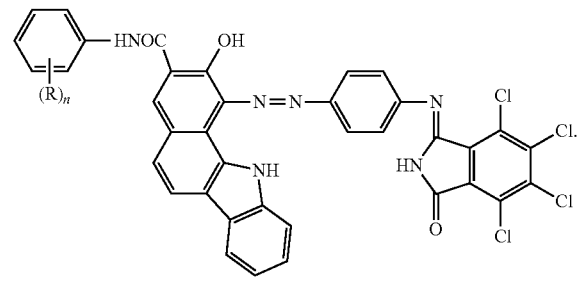

DE 19540682 discloses coating compositions for heat radiation reflecting coatings comprising at least one black pigment, at least one colour pigment, finely dispersed silicic acid and optionally white or other pigments, fillers and/or coating additives. In example 1, Chromofine® Black A 1103 (Dainichiseika, an azomethine-type pigment of undisclosed structure, having no Colour Index classification) is used.

WO 01/32 577 discloses pigmented vitreous materials, amongst which a glass plate coated with tetraethoxysilane, aqueous nitric acid and the colourant of formula

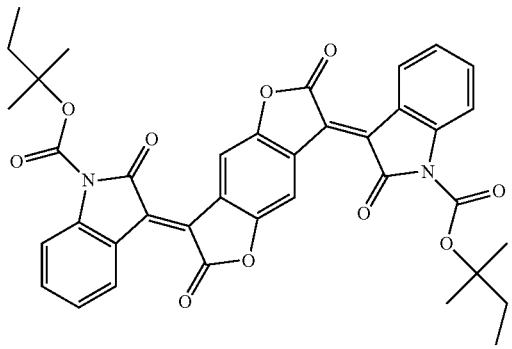 [SMILES: CCC(C)(C)OC(=O)N1C(=O)/C(=C2/C(=O)Oc3cc4c(cc32)OC(=O)/C4=C2/C(=O)N(C(=O)OC(C)(C)CC)c3ccccc32)c2ccccc21]

(example 41), which has an absorption maximum at 760-765 nm after heating to 200° C.

In spite of the advancements made in the art, there remains a need for new, stable, IR inert compositions.

SUMMARY OF THE INVENTION

It has surprisingly been found that incorporating bis-oxodihydroindolylen-benzodifuranone colourants (pigments or dyes) into plastics or coatings render the plastics or coatings NIR inert. The colourants of the present invention allow for the preparation of dark colored (including black, brown and especially grey, also brighter grey hues), NIR inert substrates.

As used herein, the term "NIR inert" means the properties of a material at wavelengths from 750 nm to 2 μm. That is, electromagnetic radiation at wavelengths from 750 nm to 2 μm is partially reflected and partially transmitted, and its energy does not or only poorly accumulate in the substrate. The NIR characteristics of articles produced according to this invention are highly advantageous in applications where heat buildup due to the absorption of NIR radiation is to be minimized or where detection by NIR sensors is to be minimized.

The same colourants, which are darkly colored, generally black or nearly black, are also found to reflect some near infra-red radiation while being transparent to much of the non-reflected NIR radiation. Incorporating the colourants into, for example, a layer which is in contact with a substrate containing a NIR absorbing material, such as a carbon black pigmented polymer, allows one to pass NIR radiation, as from a laser, through the layer containing the pigments of the invention to the underlying substrate generating enough heat at the point of irradiation to "laser weld", or melt the two materials together.

DETAILED DESCRIPTION OF THE INVENTION

A method is provided for preparing a near infra red inert organic or inorganic substrate, which method comprises the incorporation into the substrate, or the application onto the surface of the substrate, of a composition containing a bis-oxo-dihydroindolylen-benzodifuranone colourant of formula

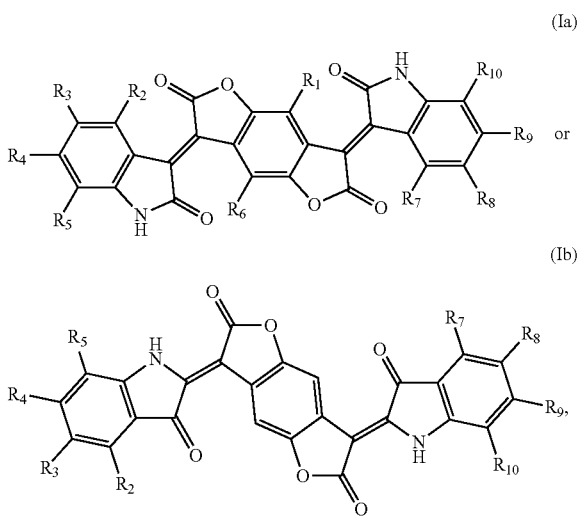

or an isomer or tautomer thereof, preferably a pigment of formulae (Ia) or (Ib) or an isomer or tautomer thereof, wherein the bis-oxodihydroindolylen-benzodifuranone colourant of formula (Ia) or (Ib) or isomer or tautomer thereof is in the form of particles of mean size ≤0.5 μm or of mean size >0.5 m and thickness ≥0.4 m which are well dispersed in the composition, in an amount effective to impart to a reflective organic or inorganic substrate an infra red reflectance of ≥20%, to a transparent organic or inorganic substrate an infra red transmittance of ≥30%, or to a semi-transparent organic or inorganic substrate a combined infra red reflectance and transmittance of ≥25%, each at wavelengths from 850 to 1600 nm, in which formulae (Ia) and (Ib)

$R_1$ and $R_6$ are each independently of the other H, $CH_3$, $CF_3$, F or Cl, preferably H or F, most preferably H;

$R_2$, $R_3$, $R_4$, $R_5$, $R_7$, $R_8$, $R_9$ and $R_{10}$ are each independently of all others H, halogen, $R_{11}$, COOH, $COOR_{11}$, $COO^-$, $CONH_2$, $CONHR_{11}$, $CONR_{11}R_{12}$, CN, OH, $OR_{11}$, $OOCR_{11}$, $OOCNH_2$, $OOCNHR_{11}$, $OOCNR_{11}R_{12}$, $NO_2$, $NH_2$, $NHR_{11}$, $NR_{11}R_{12}$, $NHCOR_{12}$, $NR_{11}COR_{12}$, $N=CH_2$, $N=CHR_{11}$, $N=CR_{11}R_{12}$, SH, $SR_{11}$, $SOR_{11}$, $SO_2R_{11}$, $SO_3R_{11}$, $SO_3H$, $SO_3^-$, $SO_2NH_2$, $SO_2NHR_{11}$ or $SO_2NR_{11}R_{12}$; whereby $R_2$ and $R_3$, $R_3$ and $R_4$, $R_4$ and $R_5$, $R_7$ and $R_8$, $R_8$ and $R_9$, and/or $R_9$ and $R_{10}$ can optionally be linked together by a direct bond or an O, S, NH or $NR_{11}$ bridge;

$R_{11}$ and $R_{12}$ are each independently of the other $C_1$-$C_{12}$alkyl, $C_1$-$C_{12}$cycloalkyl, $C_1$-$C_{12}$alkenyl, $C_1$-$C_{12}$cycloalkenyl or $C_1$-$C_{12}$alkinyl, each of which is uninterrupted or interrupted by O, NH, $NR_{13}$ and/or S in two or more fragments each comprising at least 2 C atoms, and each of which is also unsubstituted or substituted one or more times with COOH, $COOR_{13}$, $COO^-$, $CONH_2$, $CONHR_{13}$, $CONR_{13}R_{14}$, CN, O, OH, $OR_{13}$, $OOCR_{13}$, $OOCNH_2$, $OOCNHR_{13}$, $OOCNR_{13}R_{14}$, $NR_{13}$, $NH_2$, $NHR_{13}$, $NR_{13}R_{14}$, $NHCOR_{14}$, $NR_{13}COR_{14}$, $N=CH_2$, $N=CHR_{13}$, $N=CR_{13}R_{14}$, SH, $SR_{13}$, $SOR_{13}$, $SO_2R_{13}$, $SO_3R_{13}$, $SO_3H$, $SO_3—$, $SO_2NH_2$, $SO_2NHR_{13}$, $SO_2NR_{13}R_{14}$ or halogen;

or $C_7$-$C_{12}$aralkyl, $C_1$-$C_{11}$heteroaryl or $C_6$-$C_{12}$aryl, each of which is unsubstituted or substituted one or more times with COOH, $COOR_{13}$, $COO^-$, $CONH_2$, $CONHR_{13}$, $CONR_{13}R_{14}$, CN, OH, $OR_{13}$, $OOCR_{13}$, $OOCNH_2$, $OOCNHR_{13}$, $OOCNR_{13}R_{14}$, $NO_2$, $NH_2$, $NHR_{13}$, $NR_{13}R_{14}$, $NHCOR_{14}$, $NR_{13}COR_{14}$, $N=CH_2$, $N=CHR_{13}$, $N=CR_{13}R_{14}$, SH, $SR_{13}$, $SOR_{13}$, $SO_2R_{13}$, $SO_3R_{13}$, $SO_3H$, $SO_3—$, $SO_2NH_2$, $SO_2NHR_{13}$, $SO_2NR_{13}R_{14}$ or halogen; and each $R_{13}$ or $R_{14}$ is, independently of any other $R_{13}$ or $R_{14}$, $C_1$-$C_6$alkyl, benzyl or phenyl, each of which is unsubstituted or substituted one or more times with substituents as defined in the preceding paragraph, with the proviso that the total number of atoms in any substituent of $R_{13}$ and $R_{14}$ is from 1 to 8; whereby pairs of substituents selected from the group consisting of all $R_{13}$ and $R_{14}$ can optionally be linked together by a direct bond or an O, S, NH or $NR_{11}$ bridge so as to form rings.

Generally, $R_{13}$ and $R_{14}$ forming a ring are bound to the same atom, such as in $NR_{13}R_{14}$ or $CR_{13}R_{14}$. However, it is also possible $R_{13}$ and/or $R_{14}$ which are separated by 2 or more atoms to be linked together, thus forming larger rings.

When the compound of formula (Ia) or (Ib) is anionic, its charge may be compensated by any known suitable cation, for example a metallic, organic, inorganic or metal organic cation, such as preferably an alkali, earth alkali or transition metal, ammonium, primary ammonium, secondary ammonium, ternary ammonium, quaternary ammonium or an organic metal complex.

The mean size (to be calculated by particle weight) can easily be determined for example by electron microscopy or Joyce-Löbl centrifugation (such as described in EP application 07 122 749.0). The particle size distribution is most adequately determined directly from the dispersion of the colourant in a solvent and/or binder, avoiding deagglomeration of eventual remaining agglomerates by using mild conditions.

The inorganic or organic substrate may be, for example, a naturally occurring polymer or a synthetic polymer, for example a thermoplastic, elastomeric, inherently crosslinked or crosslinked polymer. For example, a method which comprises incorporating into a thermoplastic, elastomeric, crosslinked or inherently crosslinked polymer an amount of a deagglomerated bis-oxodihydroindolylen-benzodifuranone colourant of formula (Ia) or (Ib) is effective to impart to the thermoplastic, elastomeric, crosslinked or inherently crosslinked polymer an infra red reflectance of ≥20%, an infra red transmittance of ≥30%, or a combined infra red reflectance and transmittance of ≥25%, each at wavelengths from 850 to 1600 nm. Preferably, the infra red reflectance is ≥25%, the infra red transmittance is ≥40%, or the combined infra red reflectance and transmittance is ≥30%, each at wavelengths from 850 to 1600 nm. Most preferred, the infra red reflectance is ≥30%, the infra red transmittance is ≥50%, or the combined infra red reflectance and transmittance is ≥40%, each at wavelengths from 850 to 1600 nm.

The colourants of formula (Ia) or (Ib) are both reflective and transparent, however the ratio of reflectance and transmittance depends on their particle size. The reflectance (including diffracted reflectance) is much more significant with large particles, such as those having a thickness of ≥0.4 μm, while transmittance is preponderant in the case of tiny particles, such as those having a size of from 0.01 to 0.3 μm, as well as in the case of dyes which dissolve into the substrate.

The instant colourants of formula (Ia) or (Ib) are normally obtained from the synthesis in the form of very large agglomerates and aggregates of unattractive dark colours and are highly difficult to disperse, such as the violet powder obtained according to example 12b of WO 00/24 736. However, it has been found that these crude powders can easily be transformed into suitable colourants just by wet-milling them with milling aids in the presence of a solvent, preferably an alcohol, amide, ester, ether or ketone, thus obtaining particles of mean size ≤0.5 μm, preferably from 0.01 to 0.3 μm, which show surprisingly very attractive black hues similar to carbon black. Wet-milling can for example be performed in an attritor, such as a Dyno® or Netzsch® mill, Skandex® paint shaker or the like, for example using glass or ceramics (e.g. zirconia) pearls of size preferably from 0.1 to 3.0 mm, in particular from 0.5 to 1.0 mm. The amount of alcohol, amide, ester, ether or ketone is adequately from 0.1 to 1000 parts per part of colourant, preferably from 1 to 10 parts per part of colourant.

The particles of size ≤0.5 μm, preferably from 0.01 to 0.3 μm, can further be recrystallized in a polar solvent, preferably a neutral, polar liquid having a dipole moment μ of $2.8-6.0 \cdot 10^{-18}$ esu, until large particles having a thickness of ≥0.4 μm are obtained. Usually, this is done at high temperature, for example from 60 to 150° C., optionally under pressure especially above the solvent's boiling point. If desired, wet-milling and recrystallisation can be performed simultaneously, in which case it is adequate to use mild (low-shear, low-speed) wet-milling conditions towards the end of the process if large particles are desired.

Adequate solvents for wet-milling and/or recrystallisation are well-known in the art, solvents disclosed for example in EP 0 774 494, EP 0 934 364 and WO 02/068 541 being specifically incorporated herein by reference.

$R_2$, $R_4$, $R_5$, $R_7$, $R_9$, and $R_{10}$ are preferably H, F or Cl, especially H. $R_3$ and $R_8$ are preferably H, $NO_2$, $OCH_3$, $OC_2H_5$, Br, Cl, $CH_3$, $C_2H_5$, $N(CH_3)_2$, $N(CH_3)(C_2H_5)$, $N(C_2H_5)_2$, α-naphthyl, β-naphthyl or $SO_3$—. Preferably, $R_1$ is identical to $R_6$, $R_2$ is identical to $R_7$, $R_3$ is identical to $R_8$, $R_4$ is identical to $R_9$, and/or $R_5$ is identical to $R_{10}$.

$C_1$-$C_{12}$Alkyl is, for example, methyl, ethyl, n-propyl, isopropyl, n-butyl, sec-butyl, isobutyl, tert-butyl, 2-methylbutyl, n-pentyl, 2-pentyl, 3-pentyl, 2,2-dimethylpropyl, n-hexyl, heptyl, n-octyl, 1,1,3,3-tetramethylbutyl, 2-ethylhexyl, nonyl, decyl, undecyl or dodecyl.

$C_3$-$C_{12}$Cycloalkyl is, for example, cyclopropyl, cyclopropyl-methyl, cyclobutyl, cyclopentyl, cyclohexyl, cyclohexyl-methyl, trimethylcyclohexyl, thujyl, norbornyl, bornyl, norcaryl, caryl, menthyl, norpinyl, pinyl, 1-adamantyl or 2-adamantyl.

$C_2$-$C_{12}$Alkenyl is, for example, vinyl, allyl, 2-propen-2-yl, 2-buten-1-yl, 3-buten-1-yl, 1,3-butadien-2-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, or any desired isomer of hexenyl, octenyl, nonenyl, decenyl or dodecenyl.

$C_3$-$C_{12}$Cycloalkenyl is, for example, 2-cyclobuten-1-yl, 2-cyclopenten-1-yl, 2-cyclohexen-1-yl, 3-cyclohexen-1-yl, 2,4-cyclohexadien-1-yl, 1-p-menthen-8-yl, 4(10)-thujen-10-yl, 2-norbornen-1-yl, 2,5-norbornadien-1-yl, 7,7-dimethyl-2,4-norcaradien-3-yl or camphenyl.

$C_2$-$C_{12}$Alkinyl is, for example, 1-propin-3-yl, 1-butin-4-yl, 1-pentin-5-yl, 2-methyl-3-butin-2-yl, 1,4-pentadiin-3-yl, 1,3-pentadiin-5-yl, 1-hexin-6-yl, cis-3-methyl-2-penten-4-in-1-yl, trans-3-methyl-2-penten-4-in-1-yl, 1,3-hexadiin-5-yl, 1-octin-8-yl, 1-nonin-9-yl, 1-decin-10-yl or 1-dodecin-12-yl.

$C_7$-$C_{12}$Aralkyl is, for example, benzyl, 2-benzyl-2-propyl, β-phenyl-ethyl, 9-fluorenyl, α,α-dimethylbenzyl, ω-phenyl-butyl, co-phenyl-pentyl or ω-phenyl-hexyl. When $C_7$-$C_{12}$aralkyl is substituted, either the alkyl moiety or the aryl moiety of the aralkyl group can be substituted.

$C_6$-$C_{12}$Aryl is, for example, phenyl, naphthyl or 1-biphenyl.

Halogen is for example F, Cl, Br or J, preferably F on alkyl and Cl or Br on aryl.

$C_1$-$C_{11}$Heteroaryl is an unsaturated or aromatic radical having 4n+2 conjugated π-electrons, for example 2-thienyl, 2-furyl, 1-pyrazolyl, 2-pyridyl, 2-thiazolyl, 2-oxazolyl, 2-imidazolyl, isothiazolyl, triazolyl, tetrazolyl or any other ring system consisting of thiophene, furan, thiazole, oxazole, imidazole, isothiazole, thiadiazole, triazole, pyridine, pyrazine, pyrimidine, pyridazine and benzene rings and unsubstituted or substituted by from 1 to 6 ethyl substituents.

Heterocyclic groups are for example

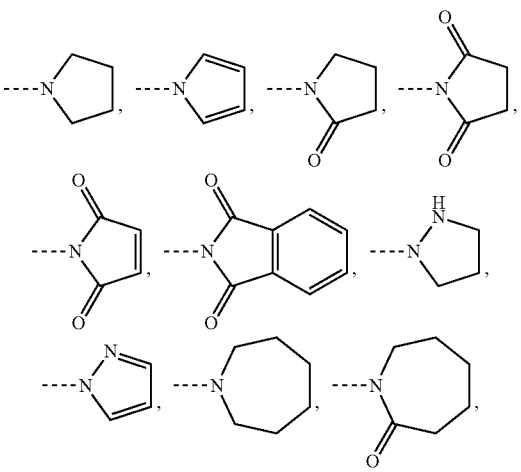

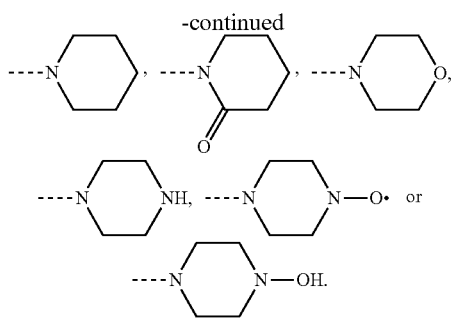

Heterocyclic groups may also be formed by linking adjacent substituents of aryl, for example

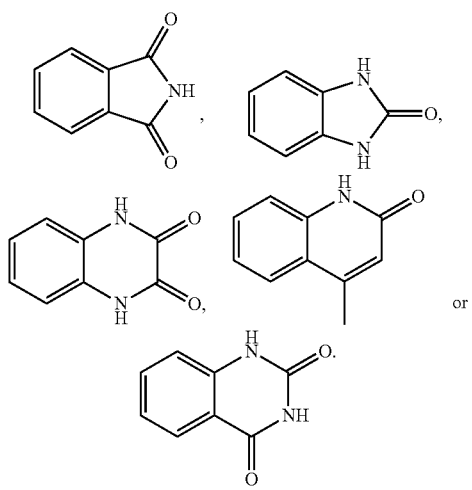

The composition containing the bis-oxodihydroindolylenbenzodifuranone colourant may be composed entirely of the pigment or dye, or of a mixture or solid solution of two or more thereof (especially from 2 to 10), or other materials as disclosed herein may also be present. Pigments and mixtures thereof are much preferred to dyes.

The bis-oxodihydroindolylen-benzodifuranone colourants of the present invention are prepared for example according or in analogy to the method disclosed in example 12b of WO00/24 736.

As used herein, the term "NIR inert" means the properties of a material at wavelengths from 750 nm to 2 µm. That is, electromagnetic radiation at wavelengths from 750 nm to 2 µm is reflected and/or transmitted. Substrates containing the present colourants, or articles coated with compositions containing the present colourants, typically have a near infra red reflectance of ≥20%, a near infra red transmittance of ≥30%, or a combined near infra red reflectance and transmittance of ≥25%, each at wavelengths from 850 to 1600 nm, in particular from 1000 to 1200 nm.

The instant compositions and substrates have the highly surprising property to show a low chroma in the visible light range (400-700 nm), preferably a saturation $C^*$ of ≤10, more preferably ≤5, most preferably ≤3. This enables to prepare superior black shades, similar to carbon black. This is not the case of known organic black colourants. Of course, it is also possible to use the colourants of formulae (Ia) or (Ib) in combination with white, black, colour, metallic or interference pigments, providing very interesting dark hues, especially grey shades, which are not obtainable by using known organic black colourants.

A particularly preferred embodiment is the use of the colourants of formulae (Ia) or (Ib) in primers, preferably grey primers. The primers of the invention comprise the colourants of formulae (Ia) or (Ib) and at least one white pigment adequately in a weight ratio of from 1:99 to 99:1, especially from 1:95 to 95:1. Suitable white pigments are listed in the Colour Index.

The grey primers of the invention preferably have a low saturation as defined above, with the additional advantage that such primer leads to a very significant lower temperature when used in combination with a basecoat comprising a low- or non-NIR-absorbing black, colour, metallic or interference pigment. Their lightness value $L^*$ is not essential, it can for example vary from about 10-20 (blackish to dark grey) over 40-60 (middle grey) up to 70-90 (very light grey) depending on the requirements for a particular purpose. The basecoat is preferably applied in 1, 2 or 3 layers directly on the primer coating and recovered by a topcoat. Preferably, this may be done by the so-called wet-on-wet process. Optionally, one or more intermediate coatings may be applied between the primer coating, the basecoat and the topcoat.

Hence, the invention also pertains to a multilayer coating comprising
 a primer coating comprising a colourant of formulae (Ia) or (Ib), or an isomer or tautomer thereof, preferably a pigment of formulae (Ia) or (Ib) or an isomer or tautomer thereof, and a white pigment in a weight ratio of from 1:99 to 99:1, especially from 1:95 to 95:1;
 a basecoat comprising a black, colour, metallic or interference pigment; and
 optionally a clear topcoat.

Such multilayer coatings are particularly advantageous for automotive bodies. When the basecoat comprises a black pigment, then such black pigment should adequately be free of carbon black and transmit or reflect infra red light. Preferably, such black pigment is or comprises a colourant of formulae (Ia) or (Ib), too.

These reflectance and transmittance characteristics are highly advantageous in applications where heat buildup due to the absorption of near infra red radiation is to be minimized and where detection by IR sensors is to be minimized. Particularly advantageously, the instant colourant of formula (Ia) or (Ib) is applied into or onto cases of devices comprising electronic components, such as laptop computers, mobile phones, walkmans or MP3 players, radio equipment, TV receivers, electronic cameras, measuring equipments such as GPS receivers, road, aerospace or other radars, telemeters, clinometers or theodolites, remote or radio controls or further electronic equipment, vehicle dashboards or automotive bodies, especially front hoods covering electronically controlled engines, air conditioners, brakes and sophisticated road-holding controls, such as ABS or EPS. An additional advantage in electronic applications is the low conductivity of materials coloured with instant colourants of formula (Ia) or (Ib).

Also advantageously, the instant colourant of formula (Ia) or (Ib) is applied into outdoor construction elements (building materials), such as roof and wall tiles, sidings, door and window frames, profiles, architectural glazing, pipes, roller or Venetian blinds, automotive, marine or aerospace parts including seats and bodies, outdoor furniture such as garden chairs and tables, or laminates on such items, artificial leather or textile materials, including in particular automotive seats as well as in yarns and fabrics of all kinds (optionally further transformed into rope, nets, awnings, felt, velvet, synthetic fur and the like), such as ceremonial or traditional dresses and other clothing (for example Tudor bonnets, square academic caps, Guardian velvet jackets, abbot hats, chadors, cassocks, shtreimels, Shinto eboshi hats and the like), or greenhouse foils, thus decreasing the deformation and aging and increasing the lifetime of such items, while increasing the comfort of use and saving energy for air conditioning. The instant low-heating materials are also much useful in camouflage applications and leisure, sports or military equipment.

The advantages in thermal heating are particularly amazing when the instant colourant of formula (Ia) or (Ib) is applied in combination with a white, low- or non-NIR-absorbing black, colour, metallic or interference pigment, for example in a weight ratio of from 1:99 to 99:1, especially from 1:95 to 95:1.

The properties of the instant colourants of formula (Ia) or (Ib) also enables to use them for optical fibers and items in contact with them.

In a further advantageous application, especially in printing inks, the instant colourant of formula (Ia) or (Ib) is applied in combination with a compound absorbing in the infra-red range from 750 nm to 2 µm, for example in a weight ratio of from 1:99 to 99:1, especially from 1:95 to 95:1. Especially useful, the instant colourant of formula (Ia) or (Ib) is printed above the compound absorbing in the infra-red range from 750 nm to 2 µm in a polychrome printing process, such as screen, offset, lithographic, flexographic, gravure or ink-jet printing processes (the details of which are well-known to the skilled artisan), onto a substrate comprising a reflective pigment, such as a white, colour, metallic or interference pigment. In this case, the reflectance of the substrate areas not printed with near infra red absorbing compound through the layer comprising the instant colourant of formula (Ia) or (Ib) is excellent, enabling identification of patterns of the near infra red absorbing compound which are invisible under daylight.

It has also been found that the instant colourant of formula (Ia) or (Ib) provides a significant improvement of the contrast when used in combination with effect pigments, in particular multi-layered interference pigments, including effect pigments which show a lightness or goniochromatic flop effect in the infra red.

Hence, the instant colourant of formula (Ia) or (Ib) provide excellent means to manufacture security or identification elements on an object by printing, especially polychrome printing, or also to calibrate printers or other devices.

For polychrome printing, the instant colourant of formula (Ia) or (Ib) is preferably incorporated into the black ink. If more than one black ink is printed, the instant colourant of formula (Ia) or (Ib) is preferably incorporated into the last printed black ink. Preferably, the near infra red absorbing compound is substantially colourless, so that a NIR absorbing pattern can be printed onto the substrate without taking account of the image to be printed ontop of it, or a coloured or black NIR absorbing compound may be used, for example carbon black, in which case the NIR absorbing pattern is printed on an area of the substrate fully to be recovered by the black ink comprising the instant colourant of formula (Ia) or (Ib).

Accordingly, the invention also relates to an item on which there is a mark showing a pattern which is different when viewed or recorded under sequential irradiation by two electromagnetic waves of different emission spectra in the range from 400 nm to 2 µm under the same or different dihedral angles to the surface of the item, or viewed or recorded under irradiation by electromagnetic waves of the same emission spectrum in the range from 400 nm to 2 m under different dihedral angles to the surface of the item, which mark comprises at least two different colourants, preferably 2, 3, 4, 5, 6, 7, 8, 9, 10 or from 11 to 25 colourants, each colourant being embedded in a wet, dry or cured ink which may be the same or different for part or all of the colourants, at least two wet, dry or cured inks preferably reflecting differently under irradiation by electromagnetic waves of emission spectrum in the range from 400 nm to 2 µm, characterized in that the mark comprises an effective amount of a colourant of formula (Ia) or (Ib), or an isomer or tautomer thereof, preferably a pigment of formulae (Ia) or (Ib) or an isomer or tautomer thereof, in at least one of the wet, dry or cured inks.

Preferably, the mark comprises a pattern comprising an infrared absorber, in addition to a different pattern comprising the instant colourant of formula (Ia) or (Ib). Infrared absorbers adequate to form well identifiable pattern are any substances having an ϵ value of about ≥5000 $mol^{-1} \cdot cm^{-1}$ at a wavelength from 715 to 2000 nm in the ink vehicle. Such infrared absorbers are well-known in the art, their chemical structure not being relevant for performing the invention.

The instant inks comprise adequately a binder and if desired a solvent and/or a curable compound as usual in the art, each of which components is usually a mixture of different compounds of the same or of different chemical classes.

The two electromagnetic waves of different spectra differ adequately when the ratio of the two quotients of the emitted energy of the first electromagnetic wave divided by the emitted energy of the second electromagnetic wave at two different wavelengths in the range from 400 nm to 2 µm is at least 3:2, preferably 10:1.

The application is performed preferably by printing, but it is also possible to apply marks by other means, such as by hand, using sequentially differently pigmented markers, for example with fountain, felt or ballpoint pens.

There may of course be multiple, identical or different marks on an item, enabling to produce both security and decorative marks, which might also be combined on the same item. The item is any object, for example but in no way restricted to a paper, cardboard or polymeric sheet, including bags and labels, a cap, seal, container of any type, including boxes, casings, or objects such as automotive and other parts, consumables such as inkjet and toner cartridges, magnetic tapes or computer readable disks such as CD-R, CD-RW, DVD+R or Blu-Ray® or similar disks.

The mark may in particular be printed on a security item such as but not restricted to identity, bank, credit or company cards, checks, banknotes, driving licenses or any other badges, pass or permits. Counterfeiting security items comprising the instant colourants of formula (Ia) or (Ib) becomes much more difficult for reasons evident to a person skilled in the art but which should of course not be disclosed herein to potential counterfeiters.

The marks may optionally be designed to be recognized automatically. In particular, this applies to bar or mosaic codes which may be hidden on an apparently plain black area. The mark is usually applied on only part of the item, for example from 0.1 to 99.9% of the item's surface, but it may also be applied uniformly on the whole item for solely decorative purposes.

The invention thus also provides a method for identifying an item, characterized in that said item comprises a mark comprising an effective amount of a colourant of formula (Ia) or (Ib), or an isomer or tautomer thereof, preferably a pigment of formulae (Ia) or (Ib) or an isomer or tautomer thereof, wherein said mark is recorded under irradiation by electromagnetic waves of wavelength from 715 to 2000 nm, and the mark's image is used for identifying the item.

Preferably, the mark's image is not apparent or different under irradiation by visible light (400-700 nm). The mark's image under infra red may be processed in usual manner visually or instrumentally and optionally converted into a visible image.

Also typically, the colourant of formula (Ia) or (Ib) is incorporated into a composition comprising a thermoplastic, thermoset, elastomeric, inherently crosslinked or crosslinked polymer. The polymer may be, for example, in the form of a film, sheet, injection-moulded article, extruded workpiece, fiber, laminate, felt or woven fabric. The polymer may also be part of a coating composition.

The dispersible colourant of formula (Ia) or (Ib) is either incorporated directly into the substrate, or applied to the surface of the substrate.

When applied to the surface of a substrate, the colourant of formula (Ia) or (Ib) may be part of a coating composition. The coating can comprise any coating system, or even a preformed film, which both adheres to the substrate and is compatible with the colourant of formula (Ia) or (Ib), for example, automotive coatings, marine coatings, paints, inks, laminates, receiving layers for printing applications, or other protective or decorative coatings including coatings or films used in glazing applications. The colourant may also be part of a fabric treatment of formula (Ia) or (Ib). Examples of thermoplastic, thermoset, elastomeric, inherently crosslinked or crosslinked polymers into which the colourants of the present invention may be incorporated into or coated onto are listed below.

1. Polymers of mono- and di-olefins, for example polypropylene, polyisobutylene, polybutene-1, poly-4-methylpentene-1, polyisoprene or polybutadiene and also polymerisates of cyclo-olefins, for example of cyclopentene or norbornene; and also polyethylene (which may optionally be crosslinked), for example high density polyethylene (HDPE), high density polyethylene of high molecular weight (HDPE-HMW), high density polyethylene of ultra-high molecular weight (HDPE-UHMW), medium density polyethylene (MDPE), low density polyethylene (LDPE), and linear low density polyethylene (LLDPE), (VLDPE) and (ULDPE).

Polyolefins, that is to say polymers of mono-olefins, as mentioned by way of example in the preceding paragraph, especially polyethylene and polypropylene, can be prepared by various processes, especially by the following methods:
a) by free radical polymerisation (usually at high pressure and high temperature);
b) by means of a catalyst, the catalyst usually containing one or more metals of group IVb, Vb, VIb or VIII. Those metals generally have one or more ligands, such as oxides, halides, alcoholates, esters, ethers, amines, alkyls, alkenyls and/or aryls, which may be either π- or α-coordinated. Such metal complexes may be free or fixed to carriers, for example to activated magnesium chloride, titanium(III) chloride, aluminium oxide or silicon oxide. Such catalysts may be soluble or insoluble in the polymerisation medium. The catalysts can be active as such in the polymerisation or further activators may be used, for example metal alkyls, metal hydrides, metal alkyl halides, metal alkyl oxides or metal alkyl oxanes, the metals being elements of group(s) Ia, IIa and/or IIIa. The activators may have been modified, for example, with further ester, ether, amine or silyl ether groups.

2. Mixtures of the polymers mentioned under 1.), for example mixtures of polypropylene with polyisobutylene, polypropylene with polyethylene (for example PP/HDPE, PP/LDPE) and mixtures of different types of polyethylene (for example LDPE/HDPE).
3. Copolymers of mono- and di-olefins with one another or with other vinyl monomers, for example ethylene/propylene copolymers, linear low density polyethylene (LLDPE) and mixtures thereof with low density polyethylene (LDPE), propylene/butene-1 copolymers, propylene/isobutylene copolymers, ethylene/butene-1 copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and copolymers thereof with carbon monoxide, or ethylene/acrylic acid copolymers and salts thereof (ionomers), and also terpolymers of ethylene with propylene and a diene, such as hexadiene, dicyclopentadiene or ethylidenenorbornene; and also mixtures of such copolymers with one another or with polymers mentioned under 1.), for example polypropylene-ethylene/propylene copolymers, LDPE-ethylene/vinyl acetate copolymers, LDPE-ethylene/acrylic acid copolymers, LLDPE-ethylene/vinyl acetate copolymers, LLDPE-ethylene/acrylic acid copolymers and alternately or randomly structured polyalkylene-carbon monoxide co-polymers and mixtures thereof with other polymers, for example polyamides.
4. Hydrocarbon resins (for example $C_5$-$C_9$) including hydrogenated modifications thereof (for example tackifier resins) and mixtures of polyalkylenes and starch.
5. Polystyrene, poly(p-methylstyrene), poly(α-methylstyrene).
6. Copolymers of styrene or α-methylstyrene with dienes or acrylic derivatives, for example styrene/butadiene, styrene/acrylonitrile, styrene/alkyl methacrylate, styrene/butadiene/alkyl acrylate and methacrylate, styrene/maleic anhydride, styrene/acrylonitrile/methyl acrylate; high-impact-strength mixtures consisting of styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene or styrene/ethylene-propylene/styrene.
7. Graft copolymers of styrene or α-methylstyrene, for example styrene on polybutadiene, styrene on polybutadiene/styrene or polybutadiene/acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleic acid imide on polybutadiene; styrene and maleic acid imide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and mixtures thereof with the copolymers mentioned under 6.), such as those known, for example, as so-called ABS, MBS, ASA or AES polymers.
8. Halogen-containing polymers, for example polychloroprene, chlorinated rubber, chlorinated and brominated copolymer of isobutylene/isoprene (halobutyl rubber), chlorinated or chlorosulfonated polyethylene, copolymers of ethylene and chlorinated ethylene, epichlorohydrin homo- and co-polymers, especially polymers of halogen-containing vinyl compounds, for example polyvinyl chloride, polyvinylidene chloride, polyvinyl fluoride, polyvinylidene fluoride; and copolymers thereof, such as vinyl chloride/vinylidene chloride, vinyl chloride/vinyl acetate or vinylidene chloride/vinyl acetate.

9. Polymers derived from ($\alpha,\beta$-unsaturated acids and derivatives thereof, such as polyacrylates and polymethacrylates, or polymethyl methacrylates, polyacrylamides and polyacrylonitriles impact-resistant-modified with butyl acrylate.

10. Copolymers of the monomers mentioned under 9.) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

11. Polymers derived from unsaturated alcohols and amines or their acyl derivatives or acetals, such as polyvinyl alcohol, polyvinyl acetate, stearate, benzoate or maleate, polyvinylbutyral, polyallyl phthalate, polyallylmelamine; and the co-polymers thereof with olefins mentioned in 1.).

12. Homo- and co-polymers of cyclic ethers, such as polyalkylene glycols, polyethylene oxide, polypropylene oxide or copolymers thereof with bisglycidyl ethers.

13. Polyacetals, such as polyoxymethylene, and also those polyoxymethylenes which contain comonomers, for example ethylene oxide; polyacetals modified with thermoplastic polyurethanes, acrylates or MBS.

14. Polyphenylene oxides and sulfides and mixtures thereof with styrene polymers or polyamides.

15. Polyurethanes derived from polyethers, polyesters and polybutadienes having terminal hydroxyl groups on the one hand and aliphatic or aromatic polyisocyanates on the other hand, and their initial products.

16. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12, 4/6, 12/12, polyamide 11, polyamide 12, aromatic polyamides derived from m-xylene, diamine and adipic acid; polyamides prepared from hexamethylenediamine and iso- and/or tere-phthalic acid and optionally an elastomer as modifier, for example poly-2,4,4-trimethylhexamethylene terephthalamide or poly-m-phenylene isophthalamide. Block copolymers of the above-mentioned polyamides with polyolefins, olefin copolymers, ionomers or chemically bonded or grafted elastomers; or with polyethers, for example with polyethylene glycol, polypropylene glycol or polytetramethylene glycol. Also polyamides or copolyamides modified with EPDM or ABS; and polyamides condensed during processing ("RIM polyamide systems").

17. Polyureas, polyimides, polyamide imides, polyether imides, polyester imides, polyhydantoins and polybenzimidazoles.

18. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates or polycaprolactone, and also block polyether esters derived from polyethers with hydroxyl terminal groups; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, urea or melamine on the other hand, such as phenol-formaldehyde, urea-formaldehyde and melamine-formaldehyde resins.

22. Drying and non-drying alkyd resins.

23. Unsaturated polyester resins derived from copolyesters of saturated and unsaturated dicarboxylic acids with polyhydric alcohols, and also vinyl compounds as crosslinking agents, and also the halogen-containing, difficultly combustible modifications thereof.

24. Crosslinkable acrylic resins derived from substituted acrylic esters, e.g. from epoxy acrylates, urethane acrylates or polyester acrylates.

25. Alkyd resins, polyester resins and acrylate resins that are crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of bisphenol-A diglycidyl ethers, bisphenol-F diglycidyl ethers, that are crosslinked using customary hardeners, e.g. anhydrides or amines with or without accelerators.

27. Natural polymers, such as cellulose, natural rubber, gelatin, or polymer-homologously chemically modified derivatives thereof, such as cellulose acetates, propionates and butyrates, and the cellulose ethers, such as methyl cellulose; and also colophonium resins and derivatives.

28. Mixtures (polyblends) of the afore-mentioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

The thermoplastic, elastomeric, crosslinked or inherently crosslinked polymer is, for example, a polyolefin, polyamide, polyurethane, polyacrylate, polyacrylamide, polyvinyl alcohol, polycarbonate, polystyrene, polyester, polyacetal, a natural or synthetic rubber or a halogenated vinyl polymer such as PVC. The polymer may be a co-polymer, a polymer blend or part of a composite. Polyamide is least preferred because some instant bis-oxodihydroindolylenbenzodifuranone colourant of formula (Ia) or (Ib) tend to dissolve therein.

The bis-oxodihydroindolylen-benzodifuranone colourants of the instant invention may be incorporated into polymer resins according a variety of known methods, provided they are in a dispersed or easy dispersible form. For example, the compounds may be added as an individual component during blending, for example, dry blending of the resin prior to processing, or the compound may be added as a blend, master batch, flush, or other concentrate in another substance prior to processing. The compounds may also be added during processing steps. Standard process steps for polymer resins are well known in the literature and include extrusion, coextrusion, compression moulding, Brabender melt processing, film formation, injection moulding, blow moulding, roto moulding, other moulding and sheet forming processes, fiber formation etc.

The dispersible compounds of formula (Ia) or (Ib) are also incorporated via dry blending, surface impregnation, suspension, dispersion and other methods known in coatings technology.

When the colourants of the instant invention are used in a film, the film is applied to the surface by, for example, the use of an adhesive, or co-extruded onto the surface. A preformed film may also be applied with heat which includes calendaring, melt applications and shrink wrapping.

When a substrate is coated with a near infra red reflecting and/or transmitting coating comprising a bis-oxodihydroindolylen-benzodifuranone colourant, the coating typically comprises a polymeric binder which can in principle be any binder customary in industry, for example those described in Ullmann's Encyclopedia of Industrial Chemistry, 5$^{th}$ Edition, Vol. A18, pp. 368-426, VCH, Weinheim 1991. In general, it is a film-forming binder based on a thermoplastic or thermosetting resin, for example, a thermosetting resin. Examples thereof are alkyd, acrylic, acrylamide, polyester, styrenic, phenolic, melamine, epoxy and polyurethane resins.

For example, non-limiting examples of common coating binders useful in the present invention include silicon containing polymers, fluorinated polymers, unsaturated polyesters, unsaturated polyamides, polyimides, crosslinkable acrylic resins derived from substituted acrylic esters, e.g. from epoxy acrylates, urethane acrylates, polyester acrylates, polymers of vinyl acetate, vinyl alcohol and vinyl amine. The coating binder polymers may be co-polymers, polymer blends or composites.

Coatings are frequently crosslinked with, for example, melamine resins, urea resins, isocyanates, isocyanurates, polyisocyanates, epoxy resins, anhydrides, poly acids and amines, with or without accelerators.

The binder can be a cold-curable or hot-curable binder. In many instances it is desirable to use bis-oxodihydroindolylen-benzodifuranone pigment rather than dye. In these instances, the binder can be a cold-curable or hot-curable binder provided that the temperature is not high enough to cause dissolution of the bis-oxodihydro-indolylen-benzodifuranone pigment; the addition of a curing catalyst may be advantageous. Suitable catalysts which accelerate curing of the binder are described, for example, in Ullmann's Encyclopedia of Industrial Chemistry, 5$^{th}$ Edition, Vol. A18, p. 469, VCH Verlagsgesellschaft, Weinheim 1991.

The binder may be a surface coating resin which dries in the air or hardens at room temperature. Exemplary of such binders are nitrocellulose, polyvinyl acetate, polyvinyl chloride, unsaturated polyester resins, polyacrylates, polyurethanes, epoxy resins, phenolic resins, and especially alkyd resins. The binder may also be a mixture of different surface coating resins. Provided the binders are curable binders, they are normally used together with a hardener and/or accelerator.

Examples of coating compositions containing specific binders are:

1. coatings based on cold- or hot-crosslinkable alkyd, acrylate, polyester, epoxy or melamine resins or mixtures of such resins, if desired with addition of a curing catalyst;
2. two-component polyurethane coatings based on hydroxyl-containing acrylate, polyester or polyether resins and aliphatic or aromatic isocyanates, isocyanurates or polyisocyanates;
3. one-component polyurethane coatings based on blocked isocyanates, isocyanurates or polyisocyanates which are deblocked during baking, if desired with addition of a melamine resin;
4. one-component polyurethane coatings based on a Tri-salkoxycarbonyltriazine crosslinker and a hydroxyl group containing resin such as acrylate, polyester or polyether resins;
5. one-component polyurethane coatings based on aliphatic or aromatic urethaneacrylates or polyurethaneacrylates having free amino groups within the urethane structure and melamine resins or polyether resins, if necessary with curing catalyst;
6. two-component coatings based on (poly)ketimines and aliphatic or aromatic isocyanates, isocyanurates or polyisocyanates;
7. two-component coatings based on (poly)ketimines and an unsaturated acrylate resin or a polyacetoacetate resin or a methacrylamidoglycolate methyl ester;
8. two-component coatings based on carboxyl- or amino-containing polyacrylates and polyepoxides;
9. two-component coatings based on acrylate resins containing anhydride groups and on a polyhydroxy or polyamino component;
10. two-component coatings based on acrylate-containing anhydrides and polyepoxides;
11. two-component coatings based on (poly)oxazolines and acrylate resins containing anhydride groups, or unsaturated acrylate resins, or aliphatic or aromatic isocyanates, isocyanurates or polyisocyanates;
12. two-component coatings based on unsaturated polyacrylates and polymalonates;
13. thermoplastic polyacrylate coatings based on thermoplastic acrylate resins or externally crosslinking acrylate resins in combination with etherified melamine resins; and
14. paint systems based on siloxane-modified or fluorine-modified acrylate resins.

Acrylic, methacrylic and acrylamide polymers and co-polymers dispersible in water are readily used as a binder in the present invention, for example, acrylic, methacrylic and acrylamide dispersion polymers and co-polymers.

For example, coatings or films comprising acrylate polymers are useful in the instant invention.

The coating composition can also comprise further components, examples being solvents, pigments, dyes, plasticizers, stabilizers, thixotropic agents, drying catalysts and/or levelling agents. Examples of possible components are those described in Ullmann's Encyclopedia of Industrial Chemistry, 5$^{th}$ Edition, Vol. A18, pp. 429-471, VCH, Weinheim 1991.

Possible drying catalysts or curing catalysts are, for example, organometallic compounds, amines, amino-containing resins and/or phosphines. Examples of organometallic compounds are metal carboxylates, especially those of the metals Pb, Mn, Co, Zn, Zr or Cu, or metal chelates, especially those of the metals Al, Ti or Zr, or organometallic compounds such as organotin compounds, for example.

Examples of metal carboxylates are the stearates of Pb, Mn or Zn, the octoates of Co, Zn or Cu, the naphthenates of Mn and Co or the corresponding linoleates, resinates or tallates.

Examples of metal chelates are the aluminium, titanium or zirconium chelates of acetylacetone, ethyl acetylacetate, salicylaldehyde, salicylaldoxime, o-hydroxy-acetophenone or ethyl trifluoroacetylacetate, and the alkoxides of these metals.

Examples of organotin compounds are dibutyltin oxide, dibutyltin dilaurate or dibutyltin dioctoate.

Examples of amines are, in particular, tertiary amines, for example tributylamine, triethanolamine, N-methyldiethanolamine, N-dimethylethanolamine, N-ethyl-morpholine, N-methylmorpholine or diazabicyclooctane (triethylenediamine) and salts thereof. Further examples are quaternary ammonium salts, for example trimethylbenzylammonium chloride.

Amino-containing resins are simultaneously binder and curing catalyst. Examples thereof are amino-containing acrylate copolymers.

The curing catalyst used can also be a phosphine, for example triphenylphosphine.

The coating compositions can also be radiation-curable coating compositions. In this case, the binder essentially comprises monomeric or oligomeric compounds containing ethylenically unsaturated bonds, which after application are cured by actinic radiation, i.e. converted into a crosslinked, high molecular weight form.

Where the system is UV-curing, it generally contains a photoinitiator as well.

Corresponding systems are described in the abovementioned publication Ullmann's Encyclopedia of Industrial Chemistry, 5$^{th}$ Edition, Vol. A18, pages 451-453. In radiation-curable coating compositions, the novel stabilizers can also be employed without the addition of sterically hindered amines.

The coating may also be a radiation-curable, solvent-free formulation of photopolymerisable compounds. Illustrative examples are mixtures of acrylates or methacrylates, unsaturated polyester/styrene mixtures or mixtures of other ethylenically unsaturated monomers or oligomers.

The coating compositions can comprise an organic solvent or solvent mixture in which the binder is soluble. The coating composition can otherwise be an aqueous solution or dispersion. The vehicle can also be a mixture of organic solvent and water. The coating composition may be a high-solids paint or can be solvent-free (e.g. a powder coating material). Powder coatings are, for example, those described in Ullmann's Encyclopedia of Industrial Chemistry, 5$^{th}$ Edition, Vol. A18, pages 438-444. The powder coating material may also have the form of a powder-slurry (dispersion of the powder preferably in water).

Multilayer systems are possible where the bis-oxodihydroindolylen-benzodifuranone colourant may reside in a coating which is then itself coated with another coating, such as a protective coating.

When used in a coating, the compounds of formula (I) are incorporated into the coating as dispersed particles via techniques common in the art. The dispersion might be combined with the incorporation into the coating composition by use of adequate solvents.

The coating composition according to the invention can be applied to any desired substrate, for example to metal, wood, plastic, composite, glass or ceramic material substrates by the customary methods, for example by brushing, spraying, pouring, draw down, spin coating, dipping or electrophoresis; see also Ullmann's Encyclopedia of Industrial Chemistry, 5$^{th}$ Edition, Vol. A18, pp. 491-500.

The bis-oxodihydroindolylen-benzodifuranone colourant as well as the white, black, colour, metallic or interference pigments are present in the instant low heating compositions independently from each other each in an "effective amount", that is an amount that provides both the desired level of coloration for the substrate or coating and also provides the desired near infra red reflectance and transmittance. For example, the bis-oxodihydroindolylen-benzodifuranone colourant, or the white, black, colour, metallic or interference pigment are present in amounts of about 0.01 to about 50% by weight of colourant of formula (Ia) or (Ib) or white, black, colour, metallic or interference pigment, based on the total weight of the composition, especially 0.01-15%, preferably 0.1-10% or especially preferred 0.1-5% by weight, based on the total weight of the composition. In the case of a coating, the composition is the fully dried and cured coating. In the case that the bis-oxodihydro-indolylen-benzodifuranone colourant and the white, black, colour, metallic or interference pigment are incorporated into different compositions, for example different layers of a multiple coating, then the percentages are based on the weight of the respective (homogeneous) compositions, rather then on the total weight of the final composite system.

It is also envisioned that when applied to the surface of a substrate, the colourant of formula (Ia) or (Ib) may be present in even higher amounts, even approaching 100%, such as in a thin layer, or a layer which is part of a laminate structure.

A composition comprising the present colourants of formula (Ia) or (Ib) may also optionally have incorporated therein or applied thereto other additives such as antioxidants, UV absorbers, hindered amine or other light stabilizers, phosphites or phosphonites, benzofuran-2-ones, thiosynergists, polyamide stabilizers, metal stearates, nucleating agents, fillers, reinforcing agents, lubricants, emulsifiers, dyes, pigments, dispersants, optical brighteners, flame retardants, antistatic agents, blowing agents and the like.

The present invention also provides a near infra red inert composition or article comprising an organic or inorganic substrate, typically a polymeric substrate, and a bis-oxodihydroindolylen-benzodifuranone colourant of formula (Ia) or (Ib), or of an isomer or tautomer thereof, preferably a pigment of formula (Ia) or (Ib) or an isomer or tautomer thereof, in an amount effective to impart to the organic or inorganic substrate an infra red reflectance of ≥20%, an infra red transmittance of ≥30%, or a combined infra red reflectance and transmittance of ≥25%, each at wavelengths from 850 to 1600 nm. The NIR inert composition or article may be a coating, film, sheet or moulded or otherwise shaped article.

For example, an infra red inert composition comprising a thermoplastic, elastomeric, crosslinked or inherently crosslinked polymer and an amount of a bis-oxodihydroindolylen-benzodifuranone colourant of formula (Ia) or (Ib) effective to impart to the composition an infra red reflectance of ≥20%, an infra red transmittance of ≥30%, or a combined infra red reflectance and transmittance of ≥25%, each at wavelengths from 850 to 1600 nm.

Also provided is a near infra red inert article comprising a substrate which is coated with a near infra red inert coating or film comprising a bis-oxodihydroindolylen-benzodifuranone colourant of formula (Ia) or (Ib).

A further embodiment of the invention provides a method for laser welding a layered article wherein a bis-oxodihydroindolylen-benzodifuranone colourant of formula (Ia) or (Ib) is incorporated into a polymeric composition which is in contact with a surface of a meltable substrate, preferably a polymeric substrate, containing a NIR absorbing material, such as a carbon black pigmented polymer, then NIR radiation, as from a laser, is passed through the layer containing the pigments of the invention to the underlying NIR absorbing material generating enough heat at the point of irradiation to "laser weld", that is melt together the two materials.

The lasers used are commonly available lasers which emit at wavelengths between about 700 and about 2000 nm, for example, between about 800 and about 1500 nm.

BRIEF DESCRIPTION OF THE DRAWINGS

FIG. 1A is a daylight picture of a sample according to example 18.

FIG. 1B shows a picture of a sample according to example 18 under infra red light exposure using a filter (passthrough 715-1000 nm).

FIG. 2 is an electronic absorption spectrum of the printed polyester substrate according to example 18, measured against blank Melinex® (reference 306, thickness 100 µm) with a Lambda™ 15 UV-VIS spectrophotometer (Perkin-Elmer).

FIG. 3A is a daylight picture of a sample according to example 19.

FIG. 3B is a picture of a sample according to example 19 under infra red light exposure using a filter (passthrough 715-1000 nm).

FIG. 1A, FIG. 1B, FIG. 3A, FIG. 3B, FIG. 4A, FIG. 5A and FIG. 5B are all colour photographic pictures which are digitalized then converted to greyscale.

Figure 4A:
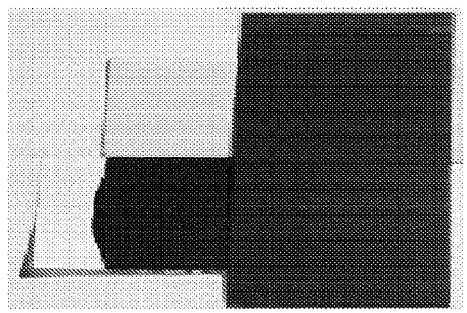
FIG. 4A is a picture of the samples setup according to example 21, wherein the print on polyester according to example 18 is laid on top of the right side of two adjacent labels, the top one printed with an IR absorber and the bottom one printed with C. I. Pigment Black 7.

The examples that follow illustrate the invention, without limiting the scope thereof (unless otherwise specified, "%" is always % by weight):

Example 1

A 12% millbase is prepared by dispersing 5.4 parts of the compound according to example 12b of WO 00/24 736 in 9.0 parts of butyl acetate for 15 minutes in a Skandex® disperser. 25.4 parts of Maprenal® MF 650 (30% in isobutanol/n-butanol/xylene 20:1:1, Solutia Inc.) are added and the mixture is dispersed again. Then, the pigment concentration is let down to 6% by adding 25.4 g cellulose acetobutyrate and 33.8 g of Dynapol® H700 and finally mixing. A layer is bar-coated on a glass plate with a 100 µm spiral bar. The transmission at 1200 nm is 68%. The CIE-colouristics are: L*=26.8, C*=1.3, h=290.2. The transmission value is enhanced to 77% by additionally using a dispersant.

Example 2

It is proceeded similarly as in example 1, with the difference that the pigment concentration is decreased to 1%. The transmission at 1200 nm is 92%.

Example 3

The compound according to example 12b of WO00/24736 is treated by wet-milling for 1 hour at 40° C. in the 10-fold amount of isopropanol (Skandex®), then filtered and dried. An easily dispersible pigment powder is obtained.

Example 4

An about 0.3 mm thick PVC sheet comprising 0.2% of the pigment powder according to example 3 is prepared in conventional manner on a two-roll mill at 150-160° C. The transmission in the wavelength range from 850 to 1600 nm varies from 65% to 83%.

Example 5

An about 0.4 mm thick flexible PVC film comprising 0.2% by weight of the pigment powder according to example 3 is prepared in conventional manner on a two-roll mill at 150-160° C. The temperature increase is determined in a heat box according to ASTM D4803-97 (2002)e1 under a commercial 250 W IR lamp. The PVC film shows about 7° C. less heat build up, as compared with a similar film containing 0.2% of commercial C Black FW 200 (Evonik, C. I. Pigment Black 7).

Example 6

Polypropylene samples comprising 0.2% of the pigment powder according to example 3 are prepared by extrusion and injection moulding at 220° C. The results are comparable to those of example 4. Especially remarkable is the disapparition of the absorption peak at around 1.2 µm, at which wavelength the transmittance (~77%) is even better than that of colourless polypropylene (~74%). The CIE-colouristics are: L*=29.1, C*=3.5, h=79.4.

Example 7

A mixture of the pigment powder according to example 3 and a LDPE-wax (1:1) is introduced at 0.1% in polypropylene (HF 420 FB, Borealis) at 260° C./56.2bar (800 psi) pressure and spun to 80 dtex/10 filaments with a stretching ratio of 1:4. A fine black yarn is obtained, which is woven to a polypropylene fabric showing about 10° C. less heat uptake and a lower NIR signature, compared with a similar fabric comprising with C. I. Pigment Black 7.

Example 8

An about 25 µm LDPE (Lupolen® 1840D, Basell) blow film thick comprising 1% of the pigment powder according to example 3 is prepared in conventional manner by extrusion and blow moulding at 200° C. The transmission in the wavelength range from 800 nm to 1500 nm varies from 87 to 90%. A comparative sample comprising commercial C Black FW 200 (Evonik) shows values of 38 to 56%.

Example 9

Polyethyleneterephthalate (PET Arnite® D04-300, DSM) samples comprising 0.02% of the pigment powder according to example 3 are prepared by extrusion and injection moulding at 280° C. The results are similar to those of example 4.

Example 10

Polymethylmethacrylate (PMMA 6N Glasklar™, Röhm GmbH, Darmstadt) samples comprising 0.05% of the pigment powder according to example 3 are prepared by extrusion and injection moulding at 200° C. The results are similar to those of example 4.

Example 11

It is proceeded similarly to example 6, with the difference that 1% of titanium white is further added to the composition. An attractive neutral grey is obtained, the saturation and the hue of which are almost identical to those of carbon black, however with a much higher reflectivity:

|  | L* | C* | h |
|---|---|---|---|
| example 5 | 67.8 | 3.6 | 246.4 |
| Pigment Black 7 | 26.5 | 3.0 | 259.9 |

Example 12

Coatings comprising the pigment powder according to example 3 are sprayed onto a steel plate onto which a primer comprising titanium white and aluminum flakes has been previously applied, giving a black appearance. The reflectance is significantly higher than that of the primer itself in the region from 800 nm to 1.35 m, and nearly identical from 1.35 µm to 1.6 µm.

Example 13

A mill base is prepared by dispersing in a Skandex® 15.0 parts of the compound according to example 12b of WO 00/24 736, 13.5 parts Ciba® EFKA®4585, 1.2 parts dimethylethanolamine (DMEA 10%), 0.3 parts Ciba® EFKA® 2550 and 70.0 parts deionized water. 2 parts of this mill base are then dispersed into 18 parts of a waterborne polyurethane-acrylate hybrid clear system (0.54 parts Maprenal® MF900 W/95, 0.8 parts Surfynol® 104E, 0.3 parts Surfynol® MD20, 0.4 parts Envirogen® AE02, 5.51 parts butylglycol, 2 parts n-butanol, 0.2 parts Dow® DC57, 3.5 parts Viscalex® HV30, 0.25 parts DMEA, 37.25 parts APU® 1012 and 49.25 parts deionized water). Coatings comprising 4% pigment on solids are sprayed onto aluminum plates and a steel plate onto which a white primer has been previously applied giving a black appearance.

Example 14

A mill base is prepared by dispersing in a Skandex® 2% of the pigment powder according to example 3 in a PES-CAB two coat system. Coatings are sprayed onto aluminum plates giving a black appearance.

Example 15

A varnish is prepared by dispersing in a Skandex® 6% of the compound according to example 12b of WO 00/24 736, nitrocellulose and alcohol. This ink is applied with a hand coater (20µ wet film thickness) onto a white substrate, on which an image has been applied using an ink comprising a slightly coloured NIR absorber. Visually, the whole sample appears grey and the image can very uneasily be distinguished. However, when the samples are photographed using an IR filter (715-1000 nm), an image is obtained which is very similar to the image before application of the compound according to example 12b of WO 00/24 736. When a perylene black is used instead of the compound according to example 12b of WO 00/24 736, violet prints are obtained instead of desirably grey prints.

Example 16

A varnish is prepared by dispersing in a Skandex® 3% of the pigment powder according to example 3 in a vinyl binder system (Movital® B20H, ethoxypropanol, methoxypropylacetate, diacetonealcohol). This ink is applied with a by hand-coater no 2 (12 µm wet film thickness) onto an aluminium foil to provide a greyish black print. When a perylene black is applied instead of the pigment powder according to example 3, violet prints are obtained instead of desirably grey prints.

Example 17 (Clear Varnish Preparation)

1 Kg of clear varnish is prepared by mild stirring at 23° C. of a formulation containing 30 g Citrofoll® BII (ATBC, Jungbunz-lauer), 150 g nitrocellulose chips AH27 containing 20% of ATBC (Christ), 10 g ethylcellulose N7 (Herkules), 40 g Kunstharz SK (Degussa), 100 g 1-ethoxypropanol, 200 g ethylacetate and 470 g ethanol. The thus obtained clear varnish has a viscosity of 18 seconds (Ford Cup n° 4).

Example 18

A nitrocellulose ink is prepared in a Skandex® by dispersing for 2 hours in a 400 ml glass bottle 15 parts of the pigment powder according to example 3 and 230 g of glass beads of 2 mm diameter into 85 parts of the clear varnish according to example 17. Application by hand-coater n° 2 (12 µm wet film thickness) on transparent polyester foil (Melinex®, reference 306, thickness 100 µm) results in a black print. Photography in daylight without filter shows an intensely coloured black image (see FIG. 1A and FIG. 2), whereas photography under infra red light using a filter (passthrough 715-1000 nm) shows a transparent colourless image of the print (see FIG. 1B).

Example 19 (Comparative)

A nitrocellulose ink is prepared by stirring with a Dispermat® at 6000 rpm for 20 minutes in a 400 ml glass bottle 25 parts Microlith® Black C-A (containing 60% C. I. Pigment Black 7), 2 parts nitrocellulose Chips AH27 (containing 20% of ATBC, Christ), 3 parts Joncryl® 68 (BASF), 5 parts Dowanol® PM (Fluka), 18 parts ethylacetate and 47 parts ethanol. Application by hand-coater n° 2 (12 µm wet film thickness) on transparent polyester foil (Melinex®, reference 306, thickness 100 µm) results in a black print. Both photographs in daylight and under infra red light using a filter (passthrough 715-1000 nm) show an intensely coloured black image (see FIG. 3A and FIG. 3B).

Example 20 (Comparative Coloristic Measurements of Examples 18 and 19)

The samples according to examples 18 and 19 are coloristically measured with CGREC for Windows Version 2.61.05. Comparative example 19 is measured against example 18 taken as reference. The shade of the print obtained according to comparative example 19 is much yellower than that according to example 18 ($\Delta H^* = 2.6$) and the colour strength of the print obtained according to comparative example 19 is 34% lower than that according to example 18:

|  |  | L* | C* | h | colour strength [%] | ΔH* |
|---|---|---|---|---|---|---|
| contrast paper | light area | 96.3 | 4.0 | 91.8 |  |  |
|  | dark area | 33.1 | 2.2 | 31.5 |  |  |

-continued

|  |  | L* | C* | h | colour strength [%] | ΔH* |
|---|---|---|---|---|---|---|
| example 18 | over light | 33.2 | 2.2 | 32.4 | 100 | — |
|  | over dark | 26.5 | 1.4 | 8.6 |  |  |
| example 19 | over light | 33.4 | 2.2 | 36.4 | 66 | 2.6 |
|  | over dark | 32.6 | 3.3 | 81.3 |  |  |

Example 21

Figure 4B:
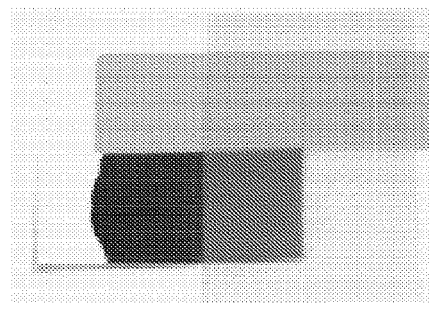
FIG. 4B is a picture of the same samples setup according to example 21 under infra red light exposure using a filter (passthrough 715-1000 nm).

The print on polyester according to example 18 is laid on top of part of two adjacent labels, the first printed with an IR absorber and the second printed with C. I. Pigment Black 7. This set up is photographed both in daylight (see FIG. 4A) and under infra red light using a filter (passthrough 715-1000 nm) (see FIG. 4B). The label printed with an IR absorber (top left) appears almost colourless under daylight and grey under IR light, but where it is covered by the print on polyester according to example 18 (top right), it is entirely masked under daylight (FIG. 4A) and appears only under IR light (FIG. 4B). The label printed with carbon black (bottom left) appears black under daylight and dark grey under IR light (likely due to some partial IR reflection), but where it is covered by the print on polyester according to example 18 (bottom right), it is entirely masked under daylight (FIG. 4A) and appears only under IR light (FIG. 4B). That is, a pattern printed for example with carbon black or another colourless or coloured IR absorber, covered with a print layer according to example 18 is hidden under daylight but clearly recognizable under infra red light using a filter (passthrough 715-1000 nm), enabling excellent marking or security applications.

Example 22

Figure 5A:
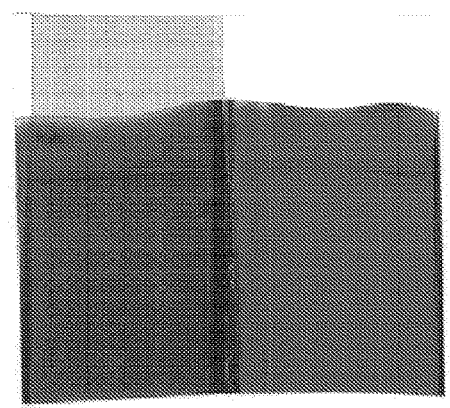
FIG. 5A is a daylight picture of the samples setup according to example 22, wherein an ink comprising the compound according to example 12b of WO 00/24 736 is printed on a paper sheet, the left half of which has previously been printed with an ink comprising an IR absorber.
Figure 5B:
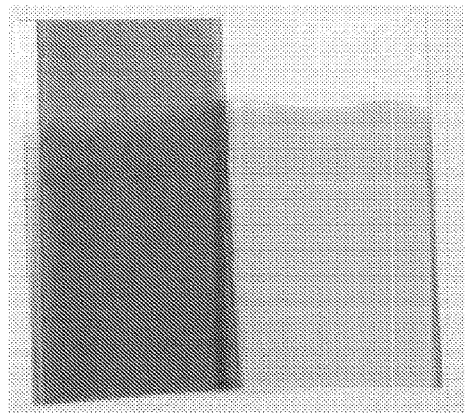
FIG. 5B is a picture of the same sample according to example 22 under infra red light exposure using a filter (passthrough 715-1000 nm).

A security element is prepared by overprinting an ink containing the pigment powder according to example 3 on top of a print containing an IR absorber. An IR absorber containing offset ink is first printed on the left half of paper sheets with a Prufbau® apparatus (1.3 g/m²). An ink according to example 18 is then applied on the bottom part of the previous print by hand-coater n° 2 (12 m wet film thickness). Photography in daylight shows almost no difference between the left part with the ink according to example 18 printed on an underlayer with the IR absorber (see FIG. 5A), whereas photography under infra red light using a filter (passthrough 715-1000 nm) reveals a large difference (see FIG. 5B).

Example 23

It is proceeded as in example 7, with the difference that the pigment powder according to example 3 is introduced at 1.0% in polypropylene and the fabric is used to manufacture camouflage nets.

Example 24

It is proceeded similarly to example 1. A millbase is prepared by dispersing 1.8 parts of the compound according to example 12b of WO00/24 736 in 3.6 parts of butyl acetate for 15 minutes in a Skandex® disperser. 26.5 parts of Maprenal® MF 650 are added and the mixture is dispersed again. Then, the pigment concentration is let down to 2% by adding 26.5 parts of cellulose acetobutyrate and 35.0 parts of Dynapol® H700 and finally mixing. A layer is bar-coated on glass with a 100 µm spiral bar. The transmission in the wavelengths from 800 to 1500 nm varies from 77% to 87%.

Example 25 (Comparative)

It is proceeded similarly to example 24, with the difference that C Black FW 200 (Evonik, C. I. Pigment Black 7) is used instead of the compound according to example 12b of WO 00/24 736. The transmission in the wavelengths from 800 to 1500 nm shows values around 22%.

Example 26

It is proceeded as in example 1, with the difference that the pigment concentration is decreased to 1%. The paint is sprayed onto aluminium plates giving a clean black appearance. A typical thermosetting acrylic top coat is then applied, which contains a combination of UV absorber and hindered amines (HALS), like for example Tinuvin® 900 and Tinuvin® 292 (both Ciba).

Example 27

A 50:50 pigment: aluminium reduction is prepared by mixing the millbase according to example 26 and an 8% aluminium base paint containing a 60% aluminium paste (Silverline® SS3334AR). The paint is sprayed onto aluminium plates giving a shiny black appearance. A typical thermosetting acrylic top coat is then applied, which contains a combination of UV absorber and hindered amines (HALS), like for example Tinuvin® 900 and Tinuvin® 292 (both Ciba).

Example 28

A 20:80 pigment: $TiO_2$ white reduction is prepared by mixing the millbase according to example 26 and a white base paint containing 20% of titanium dioxide (Kronos® 2310). The paint is sprayed onto aluminium plates giving a grey appearance. A typical thermosetting acrylic top coat is then applied, which contains a combination of UV absorber and hindered amines (HALS), like for example Tinuvin® 900 and Tinuvin® 292 (both Ciba).

Example 29

A millbase is prepared by dispersing 0.6 parts of the compound according to example 12b of WO00/24736 and titanium dioxide (Kronos® 2310) in 3.8 parts of xylene, then in 29.2 parts of an alkydmelamine lacquer based on F 310™ (60% in Solventnaphtha® 100, Bayer) and 5.0 parts of the aminoplast crosslinker Cymel® 327 (Cytec) in a Skandex® disperser. A layer is bar-coated with a 100 µm spiral bar on an aluminium plate and baken in the oven for 30 minutes at 130° C. A grey colour is obtained.

Example 30

The pigment powder according to example 3 is spun at 0.1% concentration into PES fibres (Polyester granulate GL 6105 type, Kuag Elana GmbH) at 110 dtex/24 filaments. A fine black yarn is obtained, which is weaved to a polyester fabric showing less heat uptake and a lower NIR signature as a comparable fabric comprising 0.1% C. I. Pigment Black 7.

Example 31

It is proceeded as in example 30, with the difference that the concentration of the pigment powder according to example 3 is increased to 1%.

Example 32 ('Let-Down' Clear)

A 'let-down' clear is prepared by stirring 29 parts Binder A (Bayhydrol® VPLS 2378, Bayer) and 40 parts Binder B (Bayhydrol® VPLS 2341, Bayer), then adding individually 2.5 parts butyl glycol and 6 parts n-methyl-pyrrolidone under stirring. The mixture is stirred for 15 minutes prior to further component additions. 15 parts Crosslinker A (Bayhydur® BL 5140, Bayer) and 7.5 parts Crosslinker B (Trixene® BI 7986) are added separately under stirring. The subsequent mixture is stirred for 1 hour prior to further additions to ensure all components are homogeneously mixed.

Example 33 (Titanium Dioxide Pigment Paste)

A continuous phase is prepared by mixing 38.5 parts de-ionised water, 4.2 parts of Efka® 4580 (pigment dispersant, Ciba), 0.3 parts of Efka® 2550 (antifoam agent, Ciba) and 0.4 parts of Optigel® SH (anti-settlement agent), using a disperser equipped with a Cowles blade (toothed blade). Once homogeneous, 55.0 parts titanium dioxide pigment (Kronos® 2310) are added under stirring. Once all the pigment is incorporated, the pH of the slurry is adjusted in the range 7.5 to 8.5 by use of a 10% aqueous solution of dimethylethanolamine. The slurry is then predispersed using the same disperser/Cowles blade combination for 30 minutes to ensure large pigment agglomerates are adequately 'wetted-out' in the continuous phase. The 'wetted-out' slurry is transferred to a re-circulation dispersion mill filled with zirconia grind media until maximum particle size of the dispersed pigment is ≤10 µm according to a Hegmann grind gauge.

Example 34 (Comparative Carbon Black Pigment Paste)

A continuous phase is prepared by mixing 65.7 parts deionised water, 10.0 parts of Efka® 4580 (pigment dispersant, Ciba) and 0.3 part of Efka® 2550 (antifoam agent, Ciba) with a disperser equipped with a Cowles blade (toothed blade). Once homogeneous, 12.0 parts Colour Black™ FW 200 (carbon black pigment, Evonik) are added under stirring. Once all the pigment is incorporated, the pH of the slurry is adjusted in the range 7.5 to 8.5 by use of a 10% aqueous solution of dimethylethanolamine. The slurry is then further processed as in example 33.

Example 35 (NIR-Inert Black Pigment Paste)

A continuous phase is prepared by mixing 61.2 parts deionised water, 12.5 parts of Efka® 4580 (pigment dispersant, Ciba) and 0.3 parts of Efka® 2550 (antifoam agent, Ciba) by stirring using a disperser equipped with a Cowles blade (toothed blade). Once homogeneous, 20.0 parts of the pigment powder according to example 3 are added under stirring to the continuous phase. Once all the pigment is incorporated, the pH of the slurry is adjusted in the range 7.5 to 8.5 by use of a 10% aqueous solution of dimethylethanolamine. The slurry is then further processed as in example 33.

Example 36 (Deep Grey NIR Reflective Primer; 70:30 White:Black)

To 39 parts of 'let-down' clear according to example 32, 28 parts titanium dioxide pigment paste according to example 33 and 32 parts IR-reflective black paste according to example 35 are added separately under stirring. Once all pastes are completely homogenised, 1 part of Efka® 3570 (levelling additive, Ciba) is added under stirring. The pH of the primer is adjusted by the addition of a 10% aqueous solution of dimethylethanolamine until a stable pH in the range 7.5 to 8.5 is obtained. To prepare the primer for final application, deionised water is added to the mixture until a viscosity of 30-35 seconds in a DIN 4 viscosity flow cup (23° C.) is obtained. This primer formulation is applied onto 1.0 mm thick glass panels using a drawdown bar to a dry film thickness of 40-50 µm, sufficient for full optical (visible light) opacity. After a flash off period of 30 minutes at ~23° C., the panels are pre-baked for 15 minutes at 80° C. to drive off excess water and solvent, followed by a stowing cycle of 30 minutes at 150° C. to achieve full cure.

Example 37 (Middle Grey NIR Reflective Primer; 85:15 White:Black)

To 44 parts of 'let-down' clear according to example 32, 37 parts titanium dioxide pigment paste according to example 33 and 18 parts IR-reflective black paste according to example 35 are added separately under stirring. Once all pastes are completely homogenised, 1 part of Efka® 3570 (levelling additive, Ciba) is added under stirring. The pH of the primer is adjusted by the addition of a 10% aqueous solution of dimethylethanolamine until a stable pH in the range 7.5 to 8.5 is obtained. To prepare the primer for final application, deionised water is added to the mixture until a viscosity of 30-35 seconds in a DIN 4 viscosity flow cup (23° C.) is obtained, which is then applied onto glass panels according to the procedure of example 36.

Example 38 (Black NIR-Inert Primer)

It is proceeded in analogy to example 36, with the difference that only the NIR-inert black paste according to example 35 and no titanium dioxide are used as pigments.

Example 39 (Comparative Middle Grey Primer; 95:5 White:Black)

To 46 parts of 'let-down' clear according to example 32, 43 parts titanium dioxide pigment paste according to example 33 and 11 parts carbon black pigment paste according to example 34 are added separately under stirring. Once all pastes are completely homogenised, 1 part of Efka® 3570 (levelling additive, Ciba) is added under stirring. The pH of the primer is adjusted by the addition of a 10% aqueous solution of dimethylethanolamine until a stable pH in the range 7.5 to 8.5 is obtained. To prepare the primer for final application, deionised water is added to the mixture until a viscosity of 30-35 seconds in a DIN 4 viscosity flow cup (23° C.) is obtained. This primer formulation is then applied onto 1.0 mm thick glass panels according to the procedure of example 36.

Example 40 (Comparative Black Primer)

It is proceeded according to example 36, with the difference that the carbon black pigment paste according to example 34 is used as the only pigment.

The approximative transmission and the reflection of the cured glass panels according to examples 36, 37, 38, 39 and 40 are then measured with a Lambda™ 900 UV/VIS spectrophotometer (Perkin Elmer) in the near infra-red spectral range from 700 to 1200 nm. As compared with the conventional, carbon black comprising grey primer according to comparative example 39, the grey primers according to examples 36 and 37 show about 3 to 6 times higher NIR reflectance as well as a significant NIR transmission above about 850 nm (no transmission is observed with comparative example 39 comprising carbon black). The black sample according to example 38 is also superior to the black sample according to comparative example 40 both in transmission and in reflection throughout the measured range. Above about 1000 nm, the sample according to example 38 transmits most NIR radiation and reflects a large part of the remaining, not transmitted NIR radiation, while the sample according to comparative example 40 transmits no NIR radiation and reflects about 4 times less NIR radiation than the sample according to example 38.

Similar results are obtained when the waterborne stoving formulation according to examples 32 to 40 is replaced by stoving solventborne primers and primers formulated for different curing conditions, for example ambient cured, solventborne and waterborne acrylic (and/or polyester)+ isocyanate and epoxide+polyamine, 2-component primer systems.

Example 41

According to procedures well-known to skilled artisans, the grey primer formulation according to example 37 is applied to a scale model car body by spraying. A pigmented layer comprising the pigment according to example 2 of EP application 08 157 426.1 (C. I. Pigment Yellow 139) and a clear coat, each based on coating formulations similar to and compatible with those of example 32 to 40, are then applied wet-on-wet. Curing then leads to a very uniform colouration independently of the angle of view. The model car body is then mounted on a chassis equipped with a remote control. Remote controls of relatively low heat specifications can be used without failure under sun exposure, decreasing the overall costs.

Example 42

According to procedures well-known to skilled artisans, the primer formulation according to example 36 is applied to an automotive hood by spraying (dry film thickness ~50 μm). After curing, the primer layer is overcoated by spraying first a layer of the red composition according to example 1 of EP 1 549 706 B1 (dry film thickness ~20 μm), then in a wet-on-wet process with an usual protective transparent topcoat layer comprising UV absorbers and antioxidants (dry film thickness ~50 μm). The red car hood uptakes only little heat under sun exposure and leads to enhanced durability of the coating and longer time to failure of the onboard electronic equipment (engine and brakes control systems).

The invention claimed is:

1. A method for preparing a near infra red inert organic or inorganic substrate, the method comprising:
   applying a composition onto a surface of a substrate selected from the group consisting of a reflective organic or inorganic substrate, a transparent organic or inorganic substrate, and a semi-transparent organic or inorganic substrate, the composition comprising:
   a polymeric binder; and
   a bis-oxodihydroindolylen-benzodifuranone pigment of formula

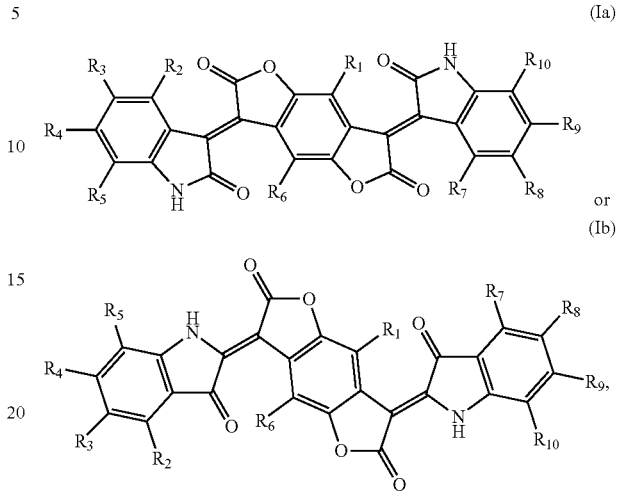

or an isomer or tautomer thereof,
wherein:
   the bis-oxodihydroindolylen-benzodifuranone pigment of formula (Ia) or (Ib) or isomer or tautomer thereof is in the form of particles (i) of mean size ≤0.5 μm or (ii) of mean size >0.5 μm and thickness ≥0.4 μm, which particles are well dispersed in the composition and are present in an amount effective to impart:
   an infra red reflectance of 20% to the resulting near infra red inert substrate when the substrate is the reflective organic or inorganic substrate,
   an infra red transmittance of ≥30% to the resulting near infra red inert substrate when the substrate is the transparent organic or inorganic substrate, or
   a combined infra red reflectance and transmittance of 25% to the resulting near infra red inert substrate when the substrate is the semi-transparent organic or inorganic substrate,
   each at wavelengths from 850 to 1600 nm;
   $R_1$ and $R_6$ are each independently of the other H or F;
   $R_2$, $R_4$, $R_5$, $R_7$, $R_9$, and $R_{10}$ are H, F, or Cl;
   $R_3$ and $R_8$ are H, $NO_2$, $OCH_3$, $OC_2H_5$, Br, Cl, $CH_3$, $C_2H_5$, $N(CH_3)_2$, $N(CH_3)(C_2H_5)$, $N(C_2H_5)_2$, α-naphthyl, β-naphthyl or $SO_3^-$;
   $R_1$ is identical to $R_6$, $R_2$ is identical to $R_7$, $R_3$ is identical to $R_8$, $R_4$ is identical to $R_9$, and/or $R_5$ is identical to $R_{10}$; and
   the amount effective of the particles is of from 0.01 to 50% by weight, based on the total weight of the composition.

2. The method according to claim 1, wherein the substrate is comprises a polymer selected from the group consisting of a thermoplastic polymer, an elastomeric polymer, and a crosslinked or inherently crosslinked polymer.

3. The method according to claim 1, wherein $R_1$ and $R_6$ are H.

4. The method according to claim 1, wherein the composition is in the form of a coating system or preformed film which both adheres to the substrate and is selected from the group consisting of an automotive coating, a marine coating, a paint, an ink, a laminate, a receiving layer for printing applications, and a protective or decorative coating for glazing applications.

5. The method according to claim 1, wherein:

the composition as applied to the substrate is in the form of a mark showing a pattern which is different when viewed or recorded under sequential irradiation by two electromagnetic waves of different emission spectra in the range from 400 nm to 2 μm under the same or different dihedral angles to the surface of the substrate, or viewed or recorded under irradiation by electromagnetic waves of the same emission spectrum in the range from 400 nm to 2 μm under different dihedral angles to the surface of the substrate, which mark comprises at least two different pigments, each pigment being embedded in a wet, dry or cured ink which may be the same or different for part or all of the pigments, at least two wet, dry or cured inks reflecting differently under irradiation by electromagnetic waves of emission spectrum in the range from 400 nm to 2 μm, and the amount effective of the particles of formula (Ia) or (Ib) or an isomer or tautomer thereof is present in at least one of the wet, dry or cured inks.

6. The method according to claim 1, wherein:

the composition as applied to the substrate is in the form of a mark identifying the substrate and comprising the pigment of formula (Ia) or (Ib) or an isomer or tautomer thereof; and applying the composition comprises recording the mark under irradiation by electromagnetic waves of wavelength from 715 to 2000 nm.

7. The method according to claim 1, wherein:

the substrate is a case of a device comprising electronic components; and the composition further comprises a white, low- or non-NTR-absorbing black, colour, metallic or interference pigment, in a weight ratio of from 1:99 to 99:1 relative to the pigment of formula (Ia) or (Ib) or isomer or tautomer thereof.

8. The method according to claim 1, wherein:

the substrate is an outdoor construction element, outdoor furniture, automotive, marine or aerospace part, laminate, artificial leather or textile material; and the composition further comprises a white, low- or non-NTR-absorbing black, colour, metallic or interference pigment, in a weight ratio of from 1:99 to 99:1 relative to the pigment of formula (Ia) or (Ib) or isomer or tautomer thereof.

9. The method according to claim 1, wherein the composition is in the form of a black ink for a polychrome printing process.

10. The method according to claim 1, wherein the composition as applied to the substrate is in the form of a film.

11. The method according to claim 2, wherein the polymer is selected from the group consisting of a polyolefin, a polyamide, a polyurethane, a polyacrylate, a polyacrylamide, a polyvinyl alcohol, a polycarbonate, a polystyrene, a polyester, a polyacetal, a natural or synthetic rubber, and a halogenated vinyl polymer.

12. The method according to claim 1, wherein the bis-oxodihydroindolylen-benzodifuranone pigment of formula (Ia) or (Ib) or isomer or tautomer thereof is in the form of particles of mean size ≤0.5 μm.

13. The method according to claim 1, wherein the bis-oxodihydroindolylen-benzodifuranone pigment of formula (Ia) or (Ib) or isomer or tautomer thereof is in the form of particles of mean size >0.5 μm and thickness ≥0.4 μm.

14. The method according to claim 1, wherein the substrate is the reflective organic or inorganic substrate, and the resulting near infra red inert substrate has an infra red reflectance of ≥20%.

15. The method according to claim 1, wherein the substrate is the transparent organic or inorganic substrate, and the resulting near infra red inert substrate has an infra red transmittance of ≥30%.

16. The method according to claim 1, wherein the substrate is the semi-transparent organic or inorganic substrate, and the resulting near infra red inert substrate has a combined infra red reflectance and transmittance of ≥25%.

17. The method according to claim 1, wherein:

the composition further comprises a white pigment in a weight ratio of from 1:99 to 99:1 relative to the pigment of formula (Ia) or (Ib) or isomer or tautomer thereof; and the method further comprises applying a basecoat to the composition as applied to the substrate, the basecoat comprising at least one of a black pigment, a color pigment, a metallic pigment, and an interference pigment.

* * * * *